United States Patent [19]

Otani et al.

[11] Patent Number: 4,457,984

[45] Date of Patent: Jul. 3, 1984

[54] CARBON ARTIFICIAL PROSTHETIC MATERIAL

[75] Inventors: Sugio Otani, 2010-2, Kurokawa, Hishi-machi, Kiryu-shi, Gumma-i, ken; Sada Katsu, Yanagisawa, 3-34-407, Mita 2-chome, Menato-Ku, Tokyo; Kunio Niijema, No. 563, Kamiko-machi, Ohmiya-shi, Saitama-ken, all of Japan

[73] Assignees: Mitsubishi Chemical Industries, Ltd., Tokyo; Sugio Otani, Kiryu; Sadakatsu Yanagisawa, Tokyo; Kunio Niijima, Ohmiya, all of Japan

[21] Appl. No.: 343,932

[22] Filed: Jan. 29, 1982

[30] Foreign Application Priority Data

Feb. 12, 1981 [JP] Japan ................................. 56-19519

[51] Int. Cl.³ ............................................. B32B 9/00
[52] U.S. Cl. .................................... 428/220; 428/244; 428/283; 428/288; 428/367; 428/368; 428/408; 433/201
[58] Field of Search ...................... 3/1, 1.9; 128/92 C; 433/201; 428/408, 312.2, 304.4, 131, 244, 288, 367, 368, 220, 283, 289, 377

[56] References Cited

U.S. PATENT DOCUMENTS 3,991,248 11/1976 Bauer .................................. 428/408
4,169,911 10/1979 Yoshida et al. ..................... 428/408
4,318,948 3/1982 Hodgson ............................ 428/408

Primary Examiner—William J. Van Balen
Attorney, Agent, or Firm—Oblon, Fisher, Spivak, McClelland & Maier

[57] ABSTRACT

An artificial prosthetic material made of a carbon source as a main component comprises a porous structure layer comprising a fibrous material and pyrolytic carbon deposited fibrous material.

5 Claims, 11 Drawing Figures

CARBON ARTIFICIAL PROSTHETIC MATERIAL

BACKGROUND OF THE INVENTION

1. Field of the Invention

The present invention relates to a prosthetic material for tooth or bone loss. More particularly, it relates to a prosthetic material which causes less tissue reaction, has high affinity and firmly locks to vital tissue and has an excellent durable hard structure and a preparation thereof.

2. Description of the Prior Art

Prosthesis of a tooth missing or an injured part of bone with an artificial material has been known since ancient times. In spite of various efforts for a long time, there still remained various problems.

As a substituent for hard tissue of a living body, metallic materials such as SUS316 stainless steel, cobalt-chromium alloy, titanium, titanium alloy, tantalum, zirconium, gold, silver, and platinum; organic hard materials such as high density polyethylene, polytetrafluoroethylene, and polymethyl methacrylate; other composites such as composite resin; and inorganic materials such as ceramics, bioglass and carbon have been studies and developed. Certain materials have been practically used.

Various characteristics are required for prosthetic materials depending upon a part for application, a configuration and a size. The applicability is different for each material.

One of the problems in the application of an artificial prosthetic material in a living body, is the loosening of the prosthesis which occurs after a certain period of time.

For example, in a repair of a fracture of bone or an artificial articulation for fixing a hard artificial prosthetic material to a bone, it has been known to employ (1) a self-locking method of fixing a prosthetic material to a bone tissue in a structural or configural form; (2) a method of mechanical fixing with a screw or spike; and (3) a method of bonding a prosthetic material to a bone with a bone cement. Thus, in these methods, certain loosening has happened for a long time and the prosthetic material must be substituted, even though the prosthetic material itself has not deteriorated.

In the other case, a dental therapy for embedding an implant in alveolar bone and fixing a crown on it to restore masticating function has been known. Various hard materials have been used as the implant material and various configurations such as screw forms, cylindrical column forms, pin forms, natural tooth root forms and blade forms have been considered depending upon the property of the material. In order to receive the masticating pressure which is highest in a living body, it is necessary to increase a contact area between the implant and the bone.

One of the inventors has studied various implants having various configurations and structures by using various materials. Certain materials do not have enough strength and other materials do not have enough affinity for a biotissue. A satisfactory material has not yet been found. Thus, the inventors have further studied and have succeeded in the preparation of an artificial prosthetic material which has superior characteristics to the conventional materials used in the prior art. The characteristics of the prosthetic materials of the present invention result from the combination of the deposition of pyrolytic carbon which imparts remarkably high strength to the prothesis and the design of a porous structure for the firm-locking of the prosthesis to the vital tissue due to the high affinity of carbon materials to vital tissue.

SUMMARY OF THE INVENTION

It is an object of the present invention to provide a carbon artificial prosthetic material which firmly locks to tissue especially bone tissue and convective tissue in a living body.

The foregoing and other objects of the present invention have been attained by providing a carbon artificial prosthetic material made of a carbon material as a main component which has a porous structure layer having a thickness of 0.1 mm or more on a surface of a substrate. The porous structure layer is formed by a pyrolytic carbon deposition and is preferably formed by using a carbon fiber, and depositing a pyrolytic carbon on the carbon fiber.

BRIEF DESCRIPTION OF THE DRAWINGS

FIG. 1 (a) shows the appearance thereof; FIG. 1 (b) shows the surface structure of the porous structure layer thereof; and FIG. 1 (c) shows the sectional view thereof;

FIG. 4 (a) shows the appearance thereof; FIG. 4 (b) shows a microscopic photography of the surface thereof; and FIG. 4 (c) shows a microscopic photograph of a sectional view; and the X part shows the porous structure layer; and the Y part shows the substrate;

FIG. 5 (a) shows the sectional view thereof and FIGS. 5 (b) shows the surface thereof;

DETAILED DESCRIPTION OF THE PREFERRED EMBODIMENTS

Figure 1B:
FIG. 1 shows microscopic photographs of the platy product in Example 1 as one example of the carbon artificial prosthetic material of the present invention.

The artificial prosthetic material of the present invention comprises a substrate made of a carbon or metal which is corrosion resistant and has high affinity to vital tissue and a surface layer made of carbon. The surface layer is a porous structure layer having a thickness of 0.1 mm or more preferably 0.3 mm or more which is remarkably important for smooth and firm locking to vital tissue.

The porous structure layer means a surface structure having high porosity and is usually a surface structure formed by fibrous material bonded each other to form pores. Various forms of the porous structure layer can be given depending upon a diameter, a length, a configuration and a content of the fibrous material, an orientation of the fibrous material and a degree of bonding. The typical structure is to randomly pile the fibrous material which is firmly bonded. The sizes of the pores are preferably 100 μm or more especially 200 μm or more in a diameter at the surface part and are reduced inside of the layer.

The artificial prosthetic material must have high resilience and strength to be durable to high impact and force. The required characteristics are effectively imparted by the porous structure layer and the deposited carbon formed by a vapor phase pyrolysis.

The artificial prosthetic material is covered with carbon formed by the vapor phase pyrolysis whereby it has excellent mechanical strength. When it is embedded in a living body, an invasion of vital tissue into the three dimensional spaces of the porous structure layer occurs and ossification of the bonded tissue results as a consequence of the bone inducing function of the carbon and the three dimensional structure of the pores a double network structure interlocking the carbon fibers with the vital tissue is formed to firmly lock the tissue to the living body.

A structure formed by rigidly bonding said members (fibrous material) is referred to as Rahmen structure (or rigid frame) in structural mechanics.

The artificial prosthetic material having a porous structure layer in Rahmen structure having three dimensional spaces has excellent advantages when it is used while repeatedly applying functional pressure such as masticating pressure.

In the porous structure layer of a Rahmen structure, ossification occurs in the deep parts to form bone tissue whereas the connective tissue remains near the surface. Collagen fiber bundles in the connective tissue is intertwined and anchored into the bone tissue. In the case of tooth, an ossification layer is formed to connect the layer to cementum by connective tissue to support an artificial tooth root as the structure of periodontal membrane. The condition of the interface between the cementum and the embedded artificial tooth root is given by the porous structure layer in Rahmen structure.

In the Rahmen structure, certain microdeformation is caused by various stresses at the part departed from the contacting part. Difference of microdeformations results in difference of qualities of the tissue by biophysical effect whereby the ossification and the connective tissue are formed. Thus, homogeneous distribution of the functional pressure is given at the interface. The Rahmen structure of the porous structure layer is the optimum structure for ideal characteristics of the formation of the double network structure and the uniform distribution of the functional pressure.

In order to prepare the novel artificial prosthetic material, the following process can be employed.

The carbon material such as various carbon fiber-reinforced carbon composition, a sintered carbon material and a glassy carbon material; or the metallic material such as platinum, titanium, tantalum and tungsten is usually fabricated in a desired form such as a rod, a plate, a blade and the other shape to form a substrate. In the case of the metallic material, if necessary, a carbon layer is coated on it by a physical vapor deposition etc.

The surface of the substrate is covered with a desired fiber to be effective for forming the porous structure layer. The fiber can be made of the carbon and the metal for the substrate and can have various forms such as woven fabric, knitting, nonwoven fabric, felt, paper and chopped strands of staple fiber. In order to cover the surface of the substrate with the fiber, in the case of the woven fabric, the knitting, the nonwoven fabric, the felt and the paper, it is cut in a desired size and is bonded with an organic binder, if necessary, it is held by winding it with yarns. In the case of the chopped strands, an organic binder is coated on the part of the surface of the substrate and the chopped strands are bonded on the part.

The processes for covering the surface of the substrate with the fiber have been described. Thus, it is preferable to employ the process for covering the substrate with a carbon fiber nonwoven fabric, if necessary, bonding it with an organic binder or fastening it by carbon fiber yarns. In such processes, it is necessary to consider the effective formation of the porous structure layer by the formation of the fiber layer having high porosity followed by the carbon deposition in the vapor phase pyrolysis.

A pyrolytic carbon is deposited on the resulting product (hereinafter referring to as a deposition material) in one-body. In the vapor phase pyrolysis, it is important for preparing excellent carbon artificial prosthetic material to deposit the carbon at a temperature of the substrate ranging from 600° C. to 2300° C. preferably 700° C. to 1100° C. in negative temperature gradient from the substrate to the surface. This condition is required for bonding the fiber layer to the surface of the substrate and forming the porous structure layer having a porosity distribution of highest density in the substrate side as the bottom of the fiber layer and gradually increased porosity from the substrate side to the outer surface. The resulting carbon artificial prosthetic material having said structure has high affinity to vital tissue to firmly lock to the vital tissue and to promote new growth of bone from the bone tissue in a living body.

In the deposition of pyrolytic carbon by the vapor phase pyrolysis, a hydrocarbon such as benzene and naphthalene and a halogenated hydrocarbon such as dichloroethane and trichloroethane can be used. When the substrate is made of carbon, high adhesiveness to the substrate is advantageously attained. When a halogenated hydrocarbon is used, the vapor phase pyrolysis is advantageously performed at a lower temperature. The vapor phase pyrolysis for the carbon deposition is depending upon the condition and is usually carried out for 1 to 10 hours.

A ratio of the pyrolytic carbon to the fibrous material in the porous structure layer is in a range of 0.01 to 50:1 preferably 1 to 35:1 especially 5 to 30:1 by weight according to microscopic observation.

The fibrous material is preferably in an intertwined form before the deposition so as to form the Rahmen structure after the deposition of pyrolytic carbon by the vapor phase pyrolysis.

In the deposition of pyrolytic carbon, a concentration of a hydrocarbon or a halogenated hydrocarbon as a carbon source gas is in a range of 0.01 to 100 vol. % preferably 0.1 to 50 vol. % especially 1 to 30 vol. %. The carrier gas is a nonoxidative gas to perform the vapor phase pyrolysis.

The embodiment of the process has been described. In modifications, it is possible to use plural kinds of nonwoven fabrics for covering the surface of the substrate to give a dense structure in the substrate side and a rough structure in the surface side and to bond them with a phenol resin binder and to carbonize them at about 1000° C. before the vapor phase pyrolysis. It is also possible to use a metallic substrate and to remove the substrate after the carbon deposition by the vapor phase pyrolysis. It is also possible to attain the purpose by covering a suitable heating body with a carbon fiber nonwoven fabric without using a substrate and forming an inner part having high packing density having a function of a substrate and a porous structure layer having a low packing density on the surface by the carbon deposition by the vapor phase pyrolysis under a condition of a temperature gradient.

The final product is obtained by grinding it, if necessary.

The carbon artificial prosthetic material of the present invention has the following characteristics.

(1) The invasion of a vital tissue, the degree of locking and the ossifying rate caused by ossification can be varied by selecting the substrate and the kind and structure of the fiber covered over the surface thereof and the size of pores to prepare products for various applications. When the surface porous structure layer has pores having a size of 10-15 μm or more, the invasion of vital tissue in the pores is resulted. When it has 100-150 μm or more, a bone tissue is formed in the pores.

(2) The prosthetic material of the present invention having a stout carbon surface formed by the carbon deposition by the vapor phase pyrolysis has antithrombogenicity and excellent affinity to vital tissue and promotes growth of a bone tissue and can be applied to various tissues.

(3) The surface is made of carbon whereby it is not corroded and has high affinity to a living body and whereby no loosening occurs even after being embedded in a living body for a long time.

(4) The porous structure layer has the Rahmen structure whereby the double network structure intertwining vital tissue with the artificial prosthetic material and the functional pressure is uniformly distributed to result in the optimum connective condition.

The applicability of the prosthetic material to vital tissue in a living body was tested by using Macacus Irus (monkey) for the evaluation.

The present invention will be further illustrated by certain examples which are provided for purposes of illustration only and are not intended to be limiting the present invention.

EXAMPLES 1: (Platy product)

A sheet of carbon fiber-reinforced carbon composition having a size of 10×10 mm and a thickness of 2.5 mm was used as a substrate and two sheets of nonwoven fabric of carbon fiber having a thickness of 0.5 mm were bonded with a small amount of phenol resin type binder to form two layers. Carbon fiber twist yarns having a diameter of about 1 mm were respectively wound in tight at each pitch of 1 mm. The resulting product is referred to as a deposition material.

Four grooves for the deposition material were caved on each surface of a graphite block having a size of 30×30×30 mm. The product is referred to as a heat sensitive graphite block. Four deposition materials were respectively held in four grooves on four surface of the graphite block to expose only each one surface of the deposition material. The other surfaces of the heat sensitive graphite block were covered with carbon fiber felt and fastened by carbon fiber yarn. The product was kept in a reactor for vapor phase pyrolysis in a high frequency induction furnace and the carbon deposition by the vapor phase pyrolysis was carried out under the following condition:

Organic material source: dichloroethylene
Carrier gas: argon
Concentration of feed gas: 13 vol. %
Feed gas flow rate: 100 ml./min.
Temperature at center of heat sensitive graphite block: 700° C.

The deposition was interrupted after the deposition for 3 hours and the deposition material was turned down and the same treatment was carried out. The intermediate product obtained by said deposition on both surfaces, had the surface carbon fiber layers bonded to the substrate in one-body by the deposited pyrolytic carbon. The fine configuration and surface condition of the intermediate product were worked by a grinder.

Figure 1C:
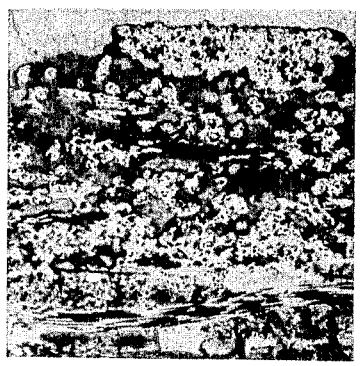
Figure 1A:

In accordance with the same process, the deposition was carried out for 1 hour for each surface to obtain a platy product of carbon artificial prosthetic material having a porous structure layer on the surfaces. FIG. 1 (a) shows the appearance of the product; FIG. 1 (b) shows the surface structure thereof and FIG. 1 (c) shows a sectional view thereof.

The nonwoven fabric of carbon fiber had a porosity of 97-98% and pyrolytic carbon was deposited at a ratio of about 8 times to carbon fiber of the nonwoven fabric according to the microscopic observation.

The platy product of the carbon artificial prosthetic material was embedded at the middle part of femur of Macacus Irus having a weight of 4 kg. After four months, bone blacks with the product were sectioned out and was sliced in a thickness of 100 μm along the surface porous structure and microradiography was taken by soft X-ray. Thus, it was found that the newly formed bone was formed in the porous structure layer near the surface (FIG. 2).

Figure 2:
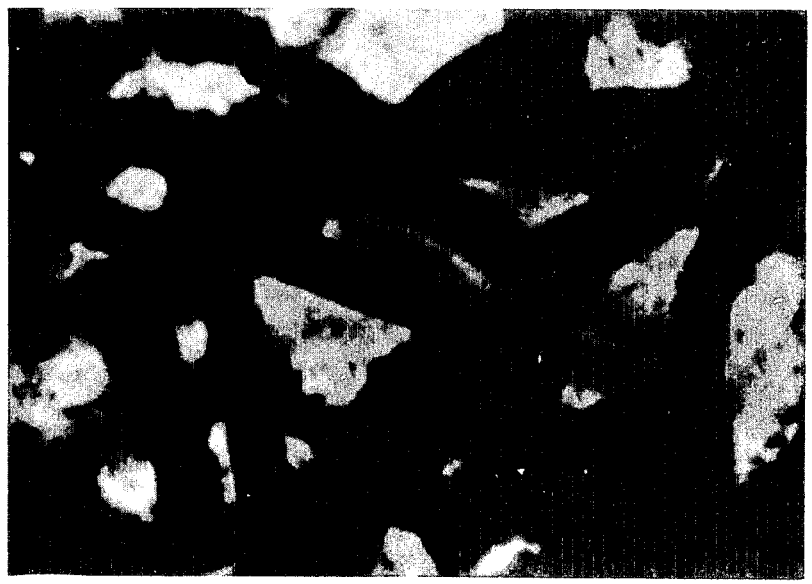
FIG. 2 is a microradiography showing the condition of invasion of the tissue in the porous structure layer of the carbon artificial prosthetic material embedded in bone.

In FIG. 2, radiolucent network structure (A) shows the carbon fiber and the radiopaque areas (B) show the bones. They are confirmed to be newly formed bones because of large lacunae (C). The shade of the part superposing to the carbon fiber is pale because the newly formed bone is present front or back of the carbon fiber. The newly formed bone is three dimensionally connected to form each double structure of carbon and bone in the interlocked form and to be firmly locked. Thus, bone was newly formed within the surface of the product and bone cells were stained by H-E stain. The fact indicates that the bone cells were alive. This fact shows that the product had excellent affinity to the tissue.

EXAMPLE 2: (Blade-form product)

Figure 3:
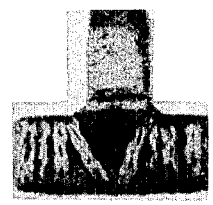
FIG. 3 shows a photograph of the appearance of blade-form implant in Example 2.

In accordance with the process of Example 1, a blade-form material was cut out from the carbon fiber-reinforced carbon sheet and the deposition material having a carbon fiber nonwoven fabric layer was produced and carbon was deposited by the vapor phase pyrolysis under the same condition to bond the surface porous structure layer to the substrate in one-body. The product shown in FIG. 3 was obtained. The product can be used as dental implant. The part shown in FIG. 3(B) is the part embedded in alveolar bone and had the surface porous structure layer. The part shown in FIG. 3(A) is the part exposed in oral cavity through epithelium and had not the porous structure layer on the surface and can be fixed to an artificial crown. The structure formed by using twist yarns placed in the outer side of the surface porous structure layer of the part B is to protect the porous structure layer. When this is not needed, the part is removed by the grinding in the working of the surfaces of the intermediate product and then, the final deposition is carried out.

The pyrolytic carbon was deposited at a ratio of about 25 times to carbon fiber of the nonwoven fabric according to the microscopic observation.

The resulting blade-form product (implant) was embedded in mandible of Macacus Irus having a weight of 4 kg. After one year, the result was excellent. The product received the masticating pressure for three teeth as an anchor of a fixed bridge without any loosening.

The epithelium tissue condition surrounding a neck of the blade-form implant was excellent without any inflammatory gingiva. No trouble had found 24 months postoperatively.

Microradio grams of an interface of alveolar bone and the functioning carbon blade implant showed that a well calcified layer was grown within the surface structure that was resembled to a cementum of natural tooth root. Histoptholgical specimens also showed that Callagen bundles in Peri-implant connective tissue were arranged functionally and anchored into both of the peripheral alveolar bone and three dimensional Porous Rahmen structure of the implant.

EXAMPLE 3: (Rod product A)

Thin paper made of carbon fiber was wound on a carbon fiberreinforced carbon rod having a diameter of 5 mm in a thickness of 0.5 mm. Five twist yarns were respectively placed in parallel to the axial direction with each equal space. The other carbon fiber yarns were respectively wound in tight to fasten the carbon fiber nonwoven fabric and the twist yarns at each pitch of 2 mm to obtain "a deposition material".

Figure 4A:
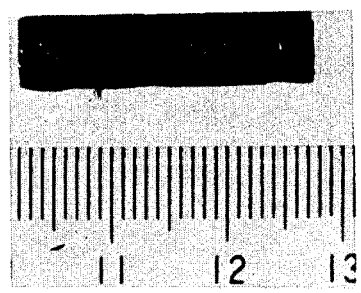
FIG. 4 shows photographs of the rod product (A) in Example 3.
Figure 4B:
Figure 4C:
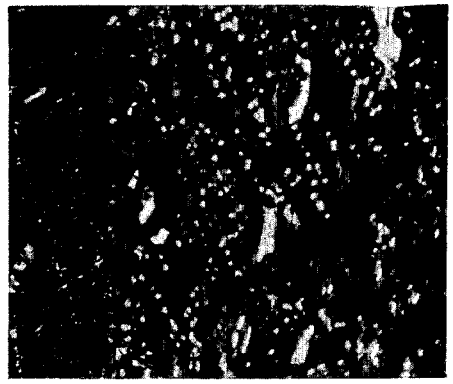

A heat sensitive graphite block was used and the central carbon fiber-reinforced carbon rod was used as the heat sensitive material and was heated by the induction furnace. A pyrolytic carbon was deposited under the condition set forth in Example 2. When the temperature of the rod at the center was 900° C., the surface temperature of the deposit material was 600° C. at the beginning of the deposition and was gradually raised. After 3 hours, the intermediate product obtained by the deposition, was treated to remove the twist yarns part wound in pitch of 2 mm by a grinder and to remain the twist yearns placed in the axial direction and then, the further deposition was carried out for 1 hour by the same process to obtain a rod product. FIG. 4 (a) shows the appearance of the product; FIG. 4 (b) shows the surface structure thereof; and FIG. 4 (c) shows the sectional view thereof. In FIG. 4 (c), the X-part shows the porous structure layer and the Y-part shows substrate.

The pyrolytic carbon was deposited at a ratio of about 15 times to carbon fiber of the nonwoven fabric according to the microscopic observation.

The rod product was cut in a length of 5 mm and the porous structure layer was reinforced with a methyl methacrylate resin composition for dental preparation and the product was placed on a cylindrical receiver having an inner diameter of 6 mm and the substrate was pressed by a cylindrical rod having a diameter of 4.5 mm to measure a shear adhesive strength between the substrate and the paper carbon fiber layer by a load cell at a pushing rate of 1 mm./min. As a result, it was 100 kg.f./cm$^2$.

The rod product was embedded in femur of Macacus Irus, After one year, the product was extracted with the bond and the adhesive strength between the surface porous structure layer and the tissue was measured by the same push-out test. It was 45 kg.f/cm$^2$. The broken part was a part of the porous structure layer with the interface.

The surgical defect of bone at the site was completely repaired and the product was kept in the same positon for one year and was fixed in the inserted site by the growth of bone in impregnation. There was not any foregin body reaction nor macrophage.

EXAMPLE 4: (Rod product B)

A paper made of carbon fiber was wound, with a small amount of a phenol resin adhesive composition, on a carbon rod having a diameter of 0.9 mm and a length of 20 cm (bending strength of 2700 kg.f./cm$^2$) in tight. Carbon fiber yarns having 3000 denier were respectively wound on the nonwoven fabric at each pitch of 2 mm to fix them and to obtain a deposition material having an outer diameter of 4 mm. The deposition material was heated by directly passing a current through the central carbon rod in the same process. The condition for depositon was as follows:

Organic source: dichloroethylene
Carrier Gas: argon
Concentration of feed gas: 28 lit.hr. (467 ml./min.)
Feed gas flow rate: 900° C.

Figure 5A:
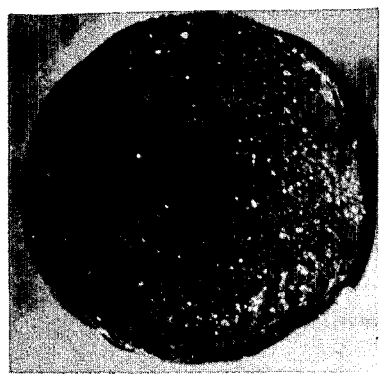
FIG. 5 shows microscopic photographs of the rod product (B) in Example 4.
Figure 5B:
Figure 6:
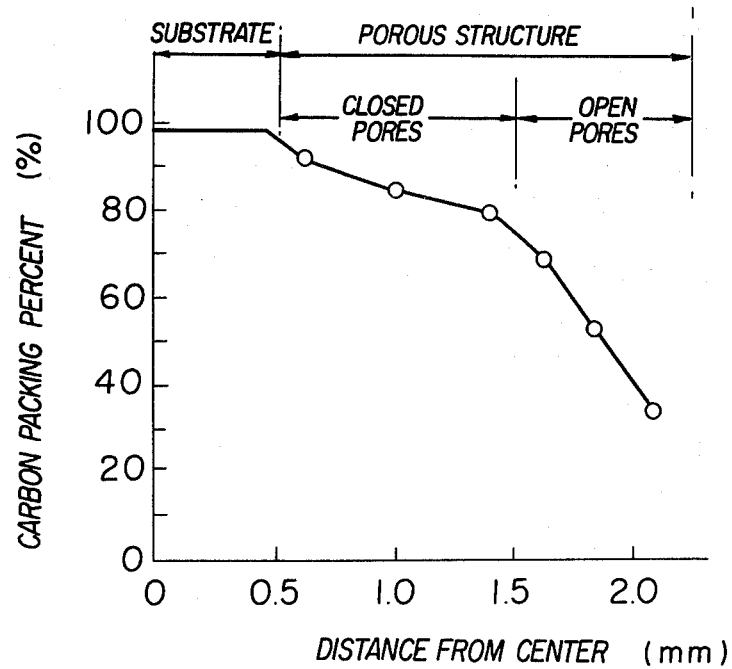
FIG. 6 is a graph showing carbon packing density (porosity in the porous structure layer) along the radial direction of the rod product in Example 4.

The temperature of the surface of the material was about 500° C. at the beginning of the deposition and was gradually raised depending upon the deposition. When it reached to 700° C. after the deposition for 12 hours, the deposition was finished. In the case of the product, the working for the intermediate product was not carried out. The resulting deposited product was cut in a desired length to obtain a rod product. FIG. 5 (a) shows the sectional view of the resulting rod product; and FIG. 5 (b) shows the surface structure. FIG. 6 shows carbon packing density along the radial direction of the product. The inside part for 1 mm in the porous structure layer had a carbon packing density of 80% or more and the pores were closed cells. The strength of the product was mainly given by the part. The pores of the outer surface layer for about 0.6 mm are open pores to form the characteristic surface porous structure layer.

The porosity of the layer was about 70% or less in the outside layer and was reduced inside as shown in FIG. 6. The rod product with the surface porous structure layer had a bending strength of about 1000 kg.f./cm$^2$.

The product was embedded in center area of femur of Macacus Irus having a weight of 4 kg.

After six months postoperation, strength of attachment between the bone and the rod product was measured by the push-out test. As a result, a shear adhesive strength was 100 kg.f./cm$^2$ at a load speed of 1 mm/min. or 145 kg.f./cm$^2$ at a load speed of 20 mm/min. Those values are greater than that between natural tooth root and alveolar bone. A fractured surface caused by the test was developed through new bone area at an interfaee between the bone and the surface structure of the product. A high porosity area of the Rahmen structure layer was ingrowed by compact bone.

We claim:
1. An artificial prosthetic material made substantially of a carbon source and having a graduated porous structure layer comprising:
   randomly piled non-woven fibrous material; and
   pyrolytic carbon deposited on the fibrous material to bond the material together; said porous structure layer having a thickness of at least about 0.1 mm and pores of at least about 100 μm in diameter at the surface and gradually reduced inside the layer.

2. The artificial prosthetic material according to claim 1 wherein said porous structure layer is formed by a deposition of pyrolytic carbon formed by a vapor phase pyrolysis.

3. The artificial prosthetic material according to claim 2 wherein the fibrous material is made of carbon fiber or metal fiber.

4. The artificial prosthetic material according to claim 1 wherein the fibrous material is bonded with a binder and carbonized before the final deposition of pyrolytic carbon.

5. The artificial prosthetic material according to claim 1, wherein said porous structure layer is placed on a substrate made of carbon or a metal as a conductive material.

* * * * *

UNITED STATES PATENT AND TRADEMARK OFFICE
CERTIFICATE OF CORRECTION

PATENT NO. : 4,457,984

DATED : July 3, 1984

INVENTOR(S) : Otani et al.

It is certified that error appears in the above-identified patent and that said Letters Patent is hereby corrected as shown below:

On the title page Item [75] should read:
- - [75] Inventors: Sugio Otani, 2010-2, Kurokawa, Hishi-machi, Kiryu-shi, Gunma-ken; Sadakatsu Yanagisawa, 3-34-407, Mita 2-chome, Minato-ku, Tokyo; Kunio Niijima, No. 563, Kamiko-machi, Ohmiya-shi, Saitama-ken, all of Japan - -

Signed and Sealed this

Fifth Day of March 1985

[SEAL]

Attest:

DONALD J. QUIGG

*Attesting Officer*  *Acting Commissioner of Patents and Trademarks*